United States Patent [19]

Richter

[11] 4,045,364

[45] Aug. 30, 1977

[54] IODOPHOR SOAP TISSUES

[75] Inventor: Ferdinand Joseph Richter, Danbury, Conn.

[73] Assignee: American Cyanamid Company, Stamford, Conn.

[21] Appl. No.: 695,226

[22] Filed: June 11, 1976

Related U.S. Application Data

[63] Continuation-in-part of Ser. No. 634,569, Nov. 24, 1975, abandoned.

[51] Int. Cl.$^2$ .................... A61K 33/18; C11D 3/48
[52] U.S. Cl. .................... 252/106; 15/104.93; 252/91; 424/16; 424/150
[58] Field of Search .................... 252/90, 91, 106; 424/16, 25, 27, 32, 80, 150; 15/104.93

[56] References Cited

U.S. PATENT DOCUMENTS

| 2,599,140 | 6/1952 | Taub | 252/107 |
|---|---|---|---|
| 2,999,265 | 9/1961 | Duane et al. | 252/91 X |
| 3,039,916 | 6/1962 | Neracher et al. | 424/150 |
| 3,138,533 | 6/1964 | Heim et al. | 252/91 X |
| 3,227,614 | 1/1966 | Scheuer | 252/91 X |
| 3,264,188 | 8/1966 | Gresham | 252/106 X |
| 3,283,357 | 11/1966 | Decker et al. | 252/91 X |
| 3,687,855 | 8/1972 | Halpern | 252/106 |
| 3,728,449 | 4/1973 | Cantor et al. | 424/150 |
| 3,950,261 | 4/1976 | Landi et al. | 252/106 |

FOREIGN PATENT DOCUMENTS 2,515,600   10/1975   Germany

*Primary Examiner*—P.E. Willis, Jr.
*Attorney, Agent, or Firm*—Neal O. Willmann; Samuel Branch Walker

[57] ABSTRACT

A disposable paper with a slightly abrasive surface impregnated with an iodophor and detergent is an excellent germicidal pre-wash in the surgical scrub routine or in any situation where it is important to impede the growth of microorganisms. By using substantially dry impregnated papers the product may be packaged and stored for at least 18 months without undue deterioration. In the presence of undue moisture, the paper degrades too fast for adequate storage.

4 Claims, No Drawings

IODOPHOR SOAP TISSUES

CROSS-REFERENCE TO RELATED APPLICATION

This application is a continuation-in-part of my earlier filed application Ser. No. 634,569 filed Nov. 24, 1975, now abandoned.

FIELD OF THE INVENTION

A disposable paper impregnated with a detergent and germicidal iodophor that is useful in any antiseptic skin cleansing procedure.

DESCRIPTION OF THE PRIOR ART

Germicidal preparations containing elemental iodine are well known. In fact, iodine is one of the oldest antiseptics known. Despite the present wide choice of available alternatives, it remains a preferred all around antiseptic of choice. Its use is preferred on the basis of efficiency, economy and low tissue toxicity.

Elemental iodine is the active germicide, but the exact manner by which iodine exerts its effect is unknown. Iodine is rapidly germicidal. In the absence of organic matter, most bacteria are killed within one minute by exposure to a 1:20,000 concentration. Slightly longer times are required to kill bacteria spores. As to its effect on other microorganisms, iodine is well known to be an effective fungicide, viricide and amebicide.

Since iodine formulations exhibit broad spectrum germicidal activity with low tissue toxicity, they are particularly useful for the antiseptic cleansing of skin.

Papers impregnated with soaps and germicides used in antiseptic skin cleansing procedures are not novel, but the art is noticeably silent on the matter of storage stable disposable papers impregnated with an antiseptic agent containing iodine.

Traub, U.S. Pat. No. 2,599,140 (1952) discloses a disinfecting composition containing glycerine, a glycol, elemental iodine, sodium iodide and sodium lauryl sulfate as a detergent.

Shelanski, U.S. Pat. No. 2,739,922 (1956) shows polyvinyl pyrrolidone-iodine complex for application to the skin. This patent in column 6, lines 11–13 recognizes corrosion of paper in the disc of the little cap. The disclosure of this patent is herein incorporated by this reference thereto.

Shelanksi et al., U.S. Pat. No. 2,931,777 (1960) discloses an iodine complex of such compounds as an ethylene oxide condensation product with nonylphenol.

Scheuer, U.S. Pat. No. 3,227,614 (1966) shows a disposable paper impregnated with a germicidal quaternary ammonium compound and detergent.

Decker et al., U.S. Pat. No. 3,283,357 (1966) shows a disposable disinfecting cleansing pad with storage capabilities which incorporates a germicidal quaternary ammonium compound and detergent activated by moistening the pad prior to use.

This apparent hiatus in the development of germicidal tissues resulted because of iodine's incompatibility with paper. With prior art formulations, iodine reacts with the paper resulting in the rapid deterioration of the product.

The present invention discloses a method of formulating iodine into a composition that can be adsorbed onto a paper, dried, packaged and stored for long periods of time, at least 18 months, without product degradation.

SUMMARY OF THE INVENTION

A dry disposable paper is impregnated with a germicidal composition comprising:
1. a nonionic detergent consisting of a series of condensates (mole wt. 5,000–10,000) of propylene oxide, propylene glycol and ethylene oxide;
2. an anionic detergent consisting of sodium N-coconut-acid-N-methyl taurate;
3. an anionic detergent consisting of a coconut-oil acid ester of sodium isethionate;
4. elemental iodine or a commercially available iodophor such as polyvinylpyrrolidone-iodine complex as the active ingredient;
5. sodium iodide, as a stabilizer;
6. isopropanol, as a solvent;
7. a weak organic acid for pH control; and using
8. water as the principal vehicle to facilitate adsorption onto the tissue surface, with subsequent removal of most of the water.

DESCRIPTION OF THE PREFERRED EMBODIMENT

The germicidal activity is provided by a product from a class of materials known as "iodophors". The term is applied to any product in which surfactants act as carriers and solubilizing agents for iodine. During the cleansing procedure, contact with water causes the iodophor to liberate iodine. The sustained release of iodine for the duration of the conventional surgical scrub prolongs the germicidal activity resulting in the removal of pathogens. Iodine harnessed as an iodophor, exhibits a reduced vapor pressure and odor. Iodophors also permit substantial dilution with water and staining is almost non-existent.

The iodophor of the present invention is prepared as follows: Water, elemental iodine, sodium iodide, isopropanol, and a weak organic acid are combined in a stainless steel vessel and agitated to effect solution. Since stability and effectiveness of the iodophor are enhanced at a lower pH, weak organic acids and salts thereof, such as citric acid or acetic acid, are added to achieve pH control in a range of about 3 to 5.5; although, the lower end of that range, about 3 to 4, is preferred. Alkalinity has been associated with the symptoms of dishpan hands. The present mildly acidic formulation is gentle to the skin under all conditions of use.

Independently, in another stainless steel vessel, a condensate of propylene oxide, propylene glycol and ethylene oxide such as Pluronic F87® is heated to form a clear molten liquid (70° ± 10° C.). While stirring the molten condensate, the iodine solution is added slowly in a very fine stream over a 2–3 hour period. The temperature of the kettle is kept at 70° ± 10° C. during the addition. Heating may be discontinued as soon as all of the solution has been added, but stirring is continued for an additional 30 minutes. This completes the preparation of the iodophor.

Although the condensate of propylene oxide, propylene glycol and ethylene oxide is a detergent and, in part, acts as such, an additional detergent-vehicle is prepared by adding water at about 40°–50° C.; a sodium N-coconut-acid-N-methyl taurate, an anionic detergent which is commercially available as Igepon TC-42®; a coconut-oil acid ester of sodium isethionate, also an anionic detergent which is commercially available as Igepon AC-78®; and a perfume such as Parento F-782®, conveniently in that order, to the prepared iodophor. This completes the preparation of the antiseptic iodophor-detergent solution which is to be impregnated into the paper.

Applicants paper is preferably prepared from long fiber virgin pulp. Paper produced from regenerated pulp usually has a lower than desired wet strength. The paper should be bland or innocuous, i.e., a minimum sulfite residue from the bleaching agents is permitted. The surface of the paper is creped to facilitate absorption of the antiseptic detergent solution and to provide a slightly abrasive surface to enhance the mechanical removal of dirt and debris. The iodophor-detergent composition is incorporated into the paper by a dip and soak procedure and the impregnated paper is then dried in a conventional steam heated oven for a period of time sufficient to remove the water content to less than about 8% by weight of the added composition.

The paper after being impregnated with the antiseptic soap solution and dried, can be packaged and stored for long periods of time, at least about 18 months, without showing signs of deterioration. Prior to use, the tissue can be interleafed "Z" folded, and stored in a suitable tissue dispenser conveniently located in lavoratories and scrub rooms. These impregnated tissues completely replace bar and liquid soaps, and since they are disposable, there is no risk of cross contamination.

A comparative study with the iodophor tissues of the present invention, Ivory® soap and tissues containing only soap, was conducted to illustrate the superior antiseptic properties of the iodophor soap tissue.

Individuals with mean baseline counts between $1.5 \times 10^6$ and $4.0 \times 10^6$ bacteria per hand were selected. The subjects were instructed not to use any products containing antimicrobials, e.g., deodorants, shampoos, creams, lotions, soaps or powders. In addition, individuals receiving antibiotic therapy or taking oral contraceptives were disqualified. Rubber gloves were issued to be worn during their daily routine whenever they came into contact with detergents, acids, bases or solvents.

Each test consisted of a pretest period, baseline period and test period.

A. Pretest Period

A period of no less than 2 weeks during which subjects did not use antimicrobial agents of any kind.

B. Baseline Period

Following the pretest period, subjects were instructed to wash their hands and ⅔ of the forearms for 30 seconds with a bland, liquid olive oil soap and deionized water at 35°–40° C. After washing, excess water was removed from the hands by shaking and loose-fitting sterile rubber gloves were donned. Fifty ml. of sampling solution (described in Table II) were added to the gloves which were fastened at the wrist. The hands were massaged for 1 minute. After massaging, a measured sample (1 ml.) was withdrawn, diluted and plated in triplicate on Trypticase Soy Agar with 0.07% lecithin and 0.5% Polysorbate 80. All plates were incubated at 37° C. for 48 hours.

C. Test Period

After 30 subjects with suitable baselines were selected, 10 were instructed to wash with the iodophor detergent tissues, 10 with Ivory soap and 10 with tissues containing only soap. Specifically, each group was instructed to wet hands and forearms under running water, saturate the tissues, if applicable, with approximately 20 cc. of water, scrub all surfaces of the hands and ⅔ of the forearms for a total of 3 minutes, and then rinse.

After testing the hands were again sampled as described in the procedure of the Baseline period. The results appear in Table I.

TABLE I

| Sample Tested | Log Baseline | Log Post-Wash | Log Net* Reduction |
|---|---|---|---|
| Ivory® Soap | 6.366 | 6.339 | 0.027 |
| Plain Soap Tissues | 6.545 | 6.470 | 0.075 |
| Iodophor-Detergent Tissues | 6.467 | 5.536 | 0.931 |

One log reduction (1.0) = 90% reduction in bacterial count.

TABLE II

| Sampling Fluid | |
|---|---|
| Potassium phosphate (monobasic) | 0.4 g. |
| Sodium phosphate (dibasic) | 10.1 g. |
| Triton X-100 | 1.0 g. |
| Distilled water to | 1 liter |

EXAMPLE 1

An iodophor detergent formulation for paper is prepared from the following ingredients:

| | Wt. % |
|---|---|
| Water | 45.4 |
| A Sodium N-coconut-acid-N-methyl taurate, e.g., Igepen TC-42® | 26.0 |
| A condensate of propylene oxide, propylene glycol and ethylene oxide, e.g., Pluronic F87® | 18.0 |
| A coconut-oil acid ester of sodium isenthionate, e.g., Igepon AC-78® | 5.0 |
| Iodine N.F. | 2.6 |
| Sodium Iodide | 1.5 |
| Citric Acid, Technical Grade | 0.2 |
| Perfume, e.g., Parento F-782 | 0.3 |

EXAMPLE 2

An iodophor detergent formulation for paper tissues can also be prepared using a commercially available iodophor.

| | Wt. % |
|---|---|
| Water | 60.5 |
| A condensate of propylene glycol, propylene oxide and ethylene oxide e.g., Pluronic F-87® | 17.0 |
| A Sodium N-coconut-acid-N-methyl taurate, e.g., Igepon TC-42® | 15.0 |
| A coconut-oil acid ester of sodium isethionate, e.g., Igepon AC-78® | 1.0 |
| Citric Acid, Technical Grade | 0.3 |
| Polyvinylpyrrolidone-iodine Complex | 6.0 |
| Perfume, Parento F-782 | .22 |
| | 100.0 |

Randomly selected iodophor detergent tissues were tested and analyzed over a period of 6 months to determine product stability. The tests were run on groups of 10 tissues and the averages were charted against the respective times. The results set forth in Table III indicate that product deterioration (if any) over the 6 months tests period was negligible.

TABLE III
ROOM TEMPERATURE STABILITY STUDIES

| Indicia of Stability | | | | | | |
|---|---|---|---|---|---|---|
| Tensile Strength, Wet Machine Direction (expressed in kg/15 mm.) | 1.61 | 1.56 | 1.47 | 1.53 | 1.35 | 1.48 |
| Tensile Strength, Dry, Machine Direction (expressed in kg/15 mm.) | 4.07 | 3.72 | 3.81 | 3.96 | 4.01 | 3.91 |
| mg.$I_2$ | 10.1 mg. | 9.07 mg. | 9.01 mg. | 8.85 mg. | 8.30 mg. | 8.37 mg. |
| Tissue Weight | 2.25 gm. | 2.23 gm. | 2.26 gm. | 2.23 gm. | 2.26 gm. | 2.23 gm. |
| | 1 mo. | 2 mo. | 3 mo. | 4 mo. | 5 mo. | 6 mo. |
| | | | TIME | | | |

What is claimed:

1. A single use wet strength paper useful in germicidal cleansing procedures impregnated with a mixture comprising:
   a. a nonionic detergent consisting of condensates of propylene oxide, propylene glycol and ethylene oxide forming a compound having a molecular weight of about 5,000 to about 10,000, about 18 parts;
   b. an anionic detergent consisting of sodium N-coconut-acid-N-methyl taurate, about 26 parts;
   c. an anionic detergent consisting of a coconut-oil acid ester of sodium isethionate, about 1 part;
   d. iodine, about 2.6 parts;
   e. sodium iodide about 1.5 parts;
   f. isopropanol about 5.0 parts;
   g. a weak organic acid, about .2 parts; and
   h. water, about 45.4 parts.

2. The single use wet strength paper of claim 1 wherein the iodine is present as a polyvinylpyrrolidone-iodine complex.

3. The single use wet strength paper of claim 1 wherein the weak organic acid is citric acid.

4. A method of preparing a storage stable iodine containing dry paper tissue comprising:
   a. combining water, about 45.4 parts; weak organic acid, about .2 parts; sodium iodide about 1.5 parts, isopropanol about 5.0 parts, and iodine 2.6 parts in a stainless steel vessel and agitating to obtain a clear solution;
   b. heating a nonionic condensate of propylene glycol, ethylene oxide and propylene oxide, about 18 parts, until melted,
   c. adding slowly the iodine solution (a) to the molten condensates (b);
   d. incorporating water, a sodium N-coconut-acid-N-methyltaurate, about 26 parts, and a coconut-oil acid ester of sodium isethionate, about 1 part, into the iodine combination (c) thereby forming an iodine-detergent composition;
   e. impregnating paper tissues with said composition; and,
   f. drying to a water content of less than about 8%.

* * * * *